(12) United States Patent
Lindström

(10) Patent No.: US 6,850,591 B2
(45) Date of Patent: Feb. 1, 2005

(54) MAMMOGRAPHY APPARATUS WITH VIBRATING COMPRESSION PLATE

(75) Inventor: Krister Lindström, Alvsjö (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/459,060

(22) Filed: Jun. 11, 2003

(65) Prior Publication Data

US 2003/0231738 A1 Dec. 18, 2003

(30) Foreign Application Priority Data

Jun. 13, 2002 (SE) .............................. 0201806

(51) Int. Cl.⁷ .............................................. A61B 6/04
(52) U.S. Cl. ........................................ 378/37; 378/208
(58) Field of Search .................... 378/37, 208

(56) References Cited

U.S. PATENT DOCUMENTS

| | | | |
|---|---|---|---|
| 5,050,197 A | | 9/1991 | Virta et al. |
| 5,335,257 A | | 8/1994 | Stunberg |
| 5,860,934 A | * | 1/1999 | Sarvazyan .................. 600/587 |
| 6,298,114 B1 | | 10/2001 | Yoda |
| 6,304,770 B1 | | 10/2001 | Lee et al. |
| 6,375,630 B1 | | 4/2002 | Cutler et al. |
| 6,577,702 B1 | * | 6/2003 | Lebovic et al. ............... 378/37 |
| 6,577,703 B2 | | 6/2003 | Lindström et al. |
| 2003/0007598 A1 | | 1/2003 | Wang et al. |

FOREIGN PATENT DOCUMENTS

| | | |
|---|---|---|
| EP | 0 370 089 | 3/1994 |
| EP | 0 435 837 | 1/1997 |
| WO | WO 98/31283 | 7/1998 |
| WO | WO 03/013358 | 2/2003 |

* cited by examiner

*Primary Examiner*—Edward J. Glick
*Assistant Examiner*—Hoon Song
(74) *Attorney, Agent, or Firm*—Schiff Hardin LLP

(57) ABSTRACT

An x-ray diagnostic device for mammogram examinations has an arm for an x-ray tube and a subject table as well as a compression plate arranged between the x-ray tube and the subject table that is connected to the arm and that is displaceable along this arm. The arm is rotatably mounted at a stand for an optimal compression of the breast with a simultaneous reduction of the pain cause by the compression, an arrangement for vibrating the compression plate during the compression procedure is provided.

7 Claims, 2 Drawing Sheets

MAMMOGRAPHY APPARATUS WITH VIBRATING COMPRESSION PLATE

BACKGROUND OF THE INVENTION

1. Field of the Invention

The present invention concerns an x-ray diagnostic device for mammography of the type having an arm for an x-ray tube and a subject table as well as a compression plate arranged between the x-ray tube and the subject table and which is displaceable along the arm, the arm being rotatably mounted to a stand.

2. Description of the Prior Art

An x-ray diagnostic device of this type is known from European Application 0 370 089. In an x-ray examination of a breast of patient, the goal is to achieve as good an image quality as possible with the least possible x-ray radiation dose. In order to achieve this, the breast to be examined is compressed, by clamping it between the subject table and the compression plate. Because the thickness of the breast is thereby decreased, the x-ray radiation dose can be reduced. The force of the compression plate against the breast is in the range of 10 to 20 kg, so the examination involves pain and unpleasantness for the patient. Some of the pain that is caused by the compression of the breast is due to the fact that the breast often adheres to the subject table and/or the compression plate, so that folds in the skin are caused on the breast. Such adhesion of the breast can also prevent the breast from evenly spreading out between the subject table and the compression plate, which also prevents an optimal reduction of the breast thickness from being achieved.

SUMMARY OF THE INVENTION

An object of the present invention is to provide an x-ray diagnostic device for mammogram examinations of the type initially described, in which an optimal compression of the breast is possible by simple means, with a simultaneous reduction in pain during the compression.

This object is achieved in accordance with the invention in a mammography device of the type initially described, having an arrangement that vibrates the compression plate during the compression procedure.

In an embodiment of the device according to the invention, vibrational arrangement is activated during a compression procedure, such that the compression plate vibrates until such time as it comes to be located in the compression position. By compression position it is meant that the compression plate has reached a position at which a mammogram should be made. The compression plate preferably begins to vibrate when it touches the breast. In a continuing compression movement, the breast is influenced by the compression plate such that it automatically spreads out as uniformly as possible on the subject table, since the breast does not adhere to the subject table and/or the compression plate due to the vibration. This also prevents skin folds in the breast from occurring. The vibration of the compression plate thus influences the thickness of the breast, such that the breast is maximally thin in the compression position, which has the advantage that the x-ray radiation dose can be kept low. The vibration ceases when the compression point is reached.

A further advantage is achieved by the vibration of the plate during compression of the breast. The vibration can bring about a stimulation of the breast, which concurrently can significantly alleviate the aforementioned feeling of discomfort that generally occurs and, above all, the pain.

According to the invention, the arrangement can be designed such that the compression plate vibrates either laterally or vertically.

In a preferred embodiment of the device according to the invention, the arrangement vibrates the compression plate laterally and vertically.

The aforementioned arrangement can be one or more motorized vibrators of a known type. Such conventional types of vibrators are described among other things in U.S. Pat. No. 6,375,630.

DESCRIPTION OF THE PREFERRED EMBODIMENTS

Figure 1:
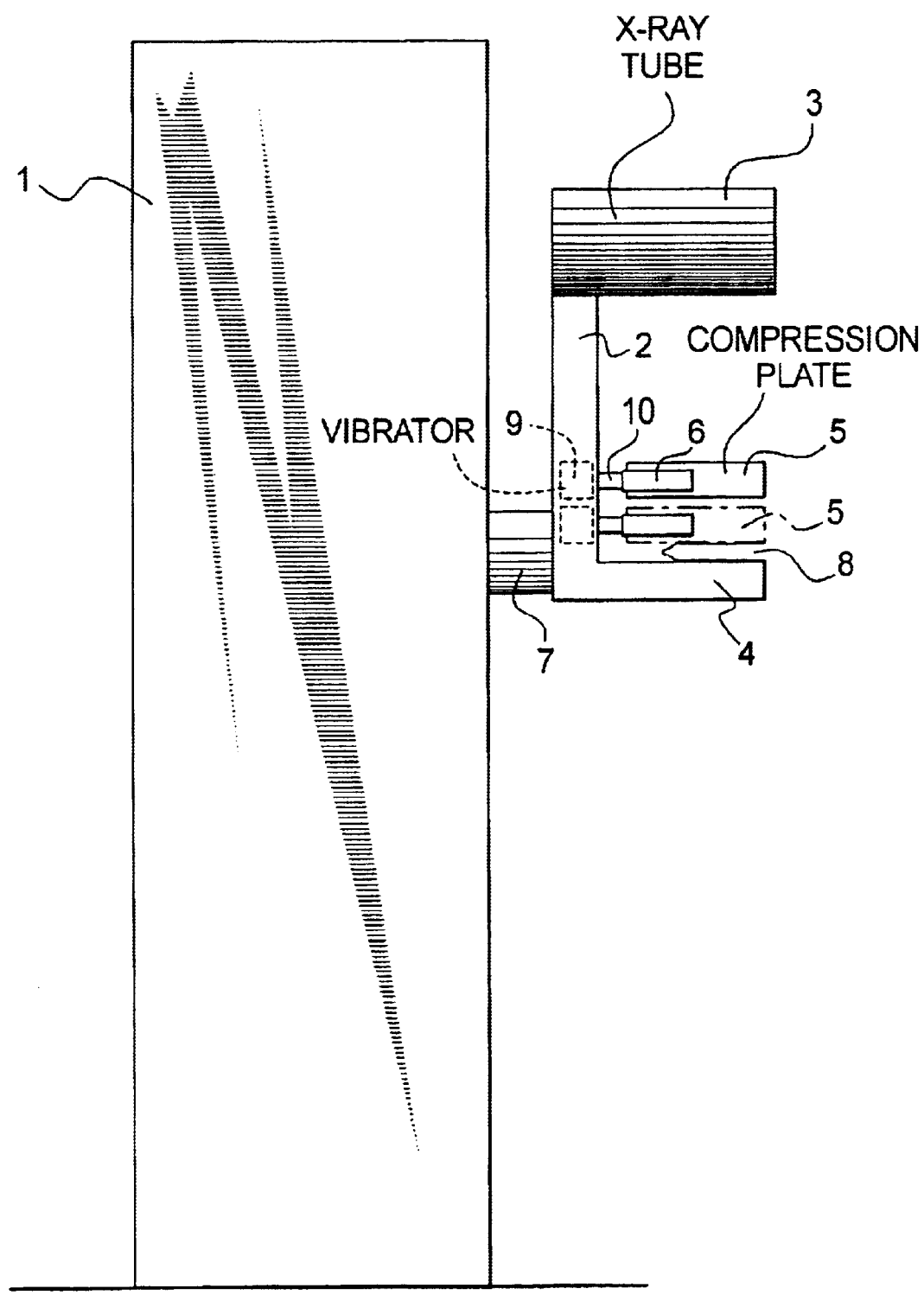
FIG. 1 is a side view of an x-ray diagnostic device according to the invention.

In FIG. 1, an x-ray diagnostic device for mammogram examinations is shown in schematic form with a stand 1 that supports an arm 2 for an x-ray tube 3 and a subject table 4. Between the x-ray tube 3 and the subject table 4, a compression plate 5 is arranged that is connected to the arm 2 by a bracket 6 and by a shaft 10, and which can be displaced along the arm 2. The arm 2 is rotatably connected to the stand 1 by a horizontal shaft 7.

In FIG. 1, the compression plate 5 is partly shown in a position between a standby position and a compression position, in which a breast 8 of a patient (not shown) would be compressed between the subject table 4 and the compression plate 5. The last position (compression position) of the compression plate 5 is indicated, in outline with dot-dash lines.

As the compression plate 5 is displaced to its compression position, the plate 5 is caused to vibrate by at least one motorized vibrator 9 that is, for example, mounted in the arm 2. The vibration preferably begins when the plate 5 touches the breast 8, and continues until the plate 5 has reached its optimal compression position. Consequently, this avoids the breast adhering to the subject table 4 or the compression plate 5, and the breast 8 is spread out in a uniform manner on the subject table 4, such that the breast is optimally thin when the compression plate 5 has reached its compression position. As already stated, an optimally thin breast allows an optimally low dose of x-ray radiation.

Figure 2:
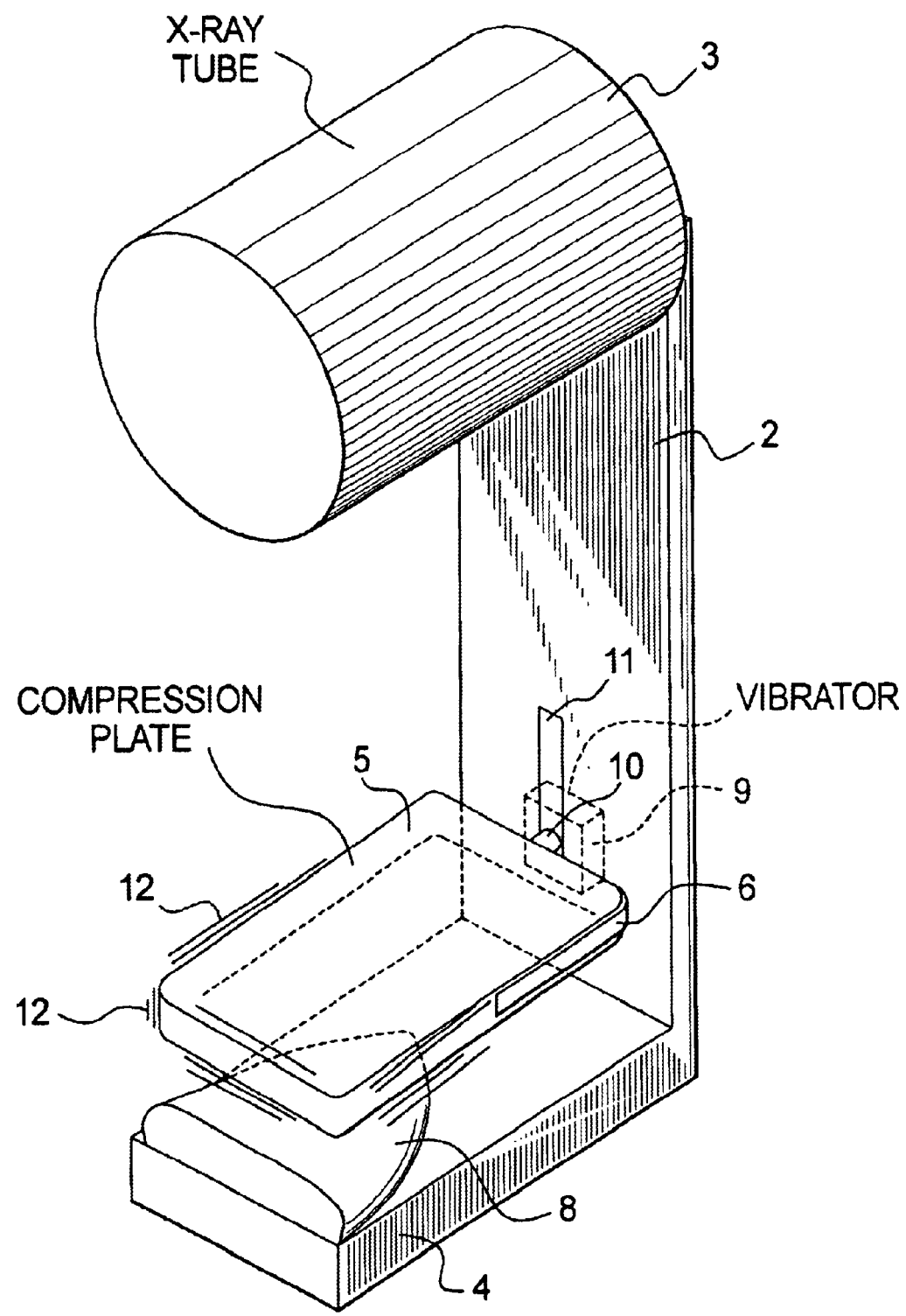
FIG. 2 is a perspective view of a part of the x-ray diagnostic device according to FIG. 1.

A perspective view of the arm 2 with the x-ray tube 3, the subject table 4, and the compression plate 5 is shown in FIG. 2. FIG. 2 shows that the shaft 10, and therewith the bracket 6 of the compression plate 5, can be displaced along the arm 2 within a slot.

The lines 12 around the compression plate 5 in FIG. 2 indicate a vibration of the plate 5 in connection with a compression of the breast 8.

The motorized vibrator 9 preferably is designed such that the compression plate 5 simultaneously vibrates laterally and vertically.

The vibrator 9 alternatively can also be designed such that the compression plate 5 vibrates either laterally or vertically.

Instead of being activated upon the composition plates touching the breast, the compression plate 5 can begin to vibrate by means of the vibrator 9 when the plate 5 leaves its aforementioned standby position, with the vibration ensuing continuously until it has reached its optimal compression position.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography apparatus comprising:
   a substantially vertical stand;
   an arm rotatably mounted to said stand;
   an x-ray tube and a subject table attached to said arm, said x-ray tube and said subject table being spaced from each other;
   a compression plate mounted to said arm so as to be movable along said arm; and
   a vibrator arrangement disposed to interact with said compression plate to vibrate said compression plate.

2. A mammography apparatus as claimed in claim 1 wherein said vibrator arrangement vibrates said compression plate laterally.

3. A mammography apparatus as claimed in claim 1 wherein said vibrator arrangement vibrates said compression plate vertically.

4. A mammography apparatus as claimed in claim 1 wherein said vibrator arrangement vibrates said compression plate laterally and vertically.

5. A mammography apparatus as claimed in claim 1 wherein said compression plate is movable in a compression procedure toward said subject table from a standby position to a compression position, and wherein said vibrator arrangement vibrates said compression plate continuously between said standby position and said compression position in said compression procedure.

6. A mammography apparatus as claimed in claim 1 wherein said compression plate is movable toward said subject table in a compression procedure from a standby position to a compression position, and wherein said vibrator arrangement stops vibrating said compression plate when said compression plate reaches said compression position.

7. A mammography apparatus as claimed in claim 1 wherein said subject table is adapted to receive a female breast thereon, and wherein said compression plate is movable from a standby position toward said breast in a compression procedure, and wherein said vibrator arrangement begins to vibrate said compression plate when said compression plate touches the breast.

* * * * *